| United States Patent [19] | [11] | 4,065,473 |
|---|---|---|
| Brossi et al. | [45] | Dec. 27, 1977 |

[54] INTERMEDIATES IN THE PREPARATION OF 2,3,4,5-TETRAHYDRO-1H-3-BENZAZEPINES

[75] Inventors: Arnold Brossi, Verona; Benjamin Pecherer, Montclair; Robert Sunbury, Wayne, all of N.J.

[73] Assignee: Hoffmann-La Roche Inc., Nutley, N.J.

[21] Appl. No.: 588,985

[22] Filed: June 20, 1975

Related U.S. Application Data

[62] Division of Ser. No. 402,536, Oct. 1, 1973, Pat. No. 3,906,006, which is a division of Ser. No. 65,340, Aug. 19, 1970, Pat. No. 3,795,683.

[51] Int. Cl.$^2$ .......................................... C07D 317/44
[52] U.S. Cl. .............................. 260/340.5 R; 424/244
[58] Field of Search ......... 260/326 A, 326 N, 562 R, 260/562 A, 326 HL, 340.5, 340.5 R

[56] References Cited

U.S. PATENT DOCUMENTS

| 2,521,813 | 9/1950 | Wachs | 260/340.5 |
|---|---|---|---|
| 3,146,266 | 8/1964 | Besendorf et al. | 260/562 A |
| 3,498,988 | 3/1970 | Houlihan et al. | 260/326 A |
| 3,520,904 | 7/1970 | Kurano et al. | 260/340.5 |
| 3,689,557 | 9/1972 | McCaully et al. | 260/562 A |
| 3,784,640 | 1/1974 | Okumura et al. | 260/340.5 |
| 3,801,601 | 4/1974 | Reinhold et al. | 260/340.5 |

*Primary Examiner*—Ethel G. Love
*Attorney, Agent, or Firm*—Samuel L. Welt; George M. Gould; Frank P. Hoffman

[57] ABSTRACT

A process for the preparation of heterocyclic compounds containing one nitrogen atom and novel 2,3,4,5-tetrahydro-1H-3-benzazepines prepared by this process are disclosed. The resulting heterocyclic compounds, including the novel 2,3,4,5-tetrahydro-1H-3-benzazepine derivatives, exhibit analgesic, appetite suppressant, and anti-edema activity.

2 Claims, No Drawings

INTERMEDIATES IN THE PREPARATION OF 2,3,4,5-TETRAHYDRO-1H-3-BENZAZEPINES

This is a division of application Ser. No. 402,536 filed Oct. 1, 1973 now U.S. Pat. No. 3,906,006, which in turn is a division of Ser. No. 65,340, filed Aug. 19, 1970, now U.S. Pat. No. 3,795,683.

DESCRIPTION OF THE INVENTION

The present invention relates to a process for preparing compounds of pharmacological value and to novel intermediates and end products resulting from this process. More particularly, the present invention relates to a process for the preparation of medium sized heterocyclic compounds containing one nitrogen atom, i.e., compounds of the formula:

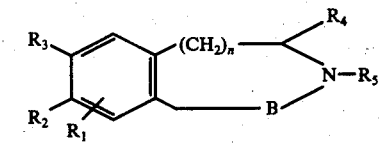

wherein $R_1$ signifies hydrogen or halogen; $R_2$ and $R_3$ each independently signify lower alkyl or lower alkoxy, or taken together signify methylenedioxy; $R_4$ signifies hydrogen, lower alkyl, carboxy, aryl, or aryl substituted by a member selected from the group consisting of halogen, lower alkyl, nitro or trifluoromethyl; $R_5$ signifies hydrogen, benzyl, lower alkyl, hydroxy-lower alkyl, lower alkyl carbonyl, halo-lower alkyl carbonyl, amino-lower alkyl carbonyl, mono-lower alkylamino-lower alkyl carbonyl, di-lower alkylamino-lower alkyl carbonyl, lower alkenyl, amino-lower alkyl, mono-lower alkylamino-lower alkyl, di-lower alkylamino-lower alkyl, carboxy-lower alkyl, carbalkoxy-lower alkyl, di-lower alkyl amino-carbonyl-lower alkyl, benzoyl-lower alkyl, halo-benzoyl-lower alkyl, or the group, —COCH$_2$R$_6$ wherein $R_6$ signifies phenyl or phenyl substituted by a member of the group consisting of halogen, lower alkyl, nitro and trifluoromethyl; $n$ is 1 or 2; and B is —CH$_2$— or —CO—
and pharmaceutically acceptable acid addition salts thereof.

As used throughout this disclosure the term "halogen" denotes all four forms thereof, i.e., chlorine, fluorine, bromine and iodine unless otherwise specified. The term "lower alkyl" includes straight and branched chain hydrocarbon groups having from 1 to 7, preferably 1 to 4 carbon atoms including, for example, methyl, ethyl, propyl, isopropyl, butyl and the like. Likewise, the term "lower alkenyl" includes straight and branched chain olefinic unsaturated hydrocarbon groups having from 2 to 7, preferably from 2 to 4 carbon atoms. The phrase "carbalkoxy" signifies the grouping —COO—lower alkyl. The expression "halolower alkyl" includes mono as well as di- and tri-halo lower alkyl groups. The term "aryl" denotes an organic radical derived from an aromatic hydrocarbon by the removal of a hydrogen atom. The term "acyl" is intended to denote an organic radical derived by removal of (a) hydroxyl groups(s) from an organic acid(s).

The process of the present invention results in the preparation of many novel heterocyclic compounds, including, of particular interest, many heretofor unknown 2,3,4,5-tetrahydro-1H-3-benzazepine derivatives (hereinafter referred to as 3-benzazepines). Among the preferred novel 3-benzazepines prepared according to this invention are those wherein the phenyl ring bears a methylenedioxy group in positions 7,8. Another preferred group of novel 3-benzazepines prepared following the inventive procedure consists of compounds showing substitution on the 3-nitrogen. Of particular interest among the novel 3-benzazepines of this invention are compounds of the formula:

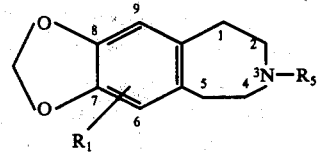

wherein $R_1$ and $R_5$ are as described above and pharmaceutically acceptable acid addition salts thereof. The 3-benzazepines of formula II above are novel and as such form a part of the present invention.

The numbering of the 3-benzazepine ring system used in this disclosure is shown in formula II above.

A preferred class of compounds falling within the scope of formula II above are those wherein $R_5$ signifies hydrogen, lower alkyl, hydroxy-lower alkyl, amino-lower alkyl, mono-lower alkyl-amino-lower alkyl and di-lower alkylamino-lower alkyl, i.e., compounds of the formula:

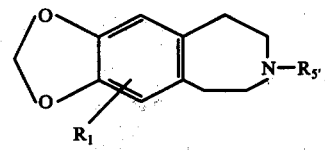

wherein $R_1$ is as described above; and $R_5'$ signifies hydrogen, lower alkyl, hydroxy-lower alkyl, amino-lower alkyl, mono-lower alkylamino-lower alkyl, di-lower alkylamino-lower alkyl
and pharmaceutically acceptable acid addition salts thereof.

Another preferred class of compounds falling within the scope of formula II are those wherein $R_5$ signifies lower alkyl carbonyl, halo-lower alkyl carbonyl, amino-lower alkyl carbonyl, mono-lower alkyl-amino-lower alkyl carbonyl, di-lower alkylamino-lower alkyl carbonyl and the group —COCH$_2$R$_6$, R$_6$ being as described above, i.e., compounds of the formula:

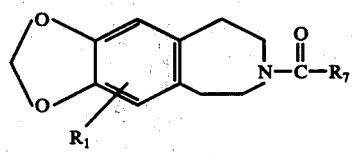

wherein $R_1$ is as described above and $R_7$ signifies lower alkyl, halo-lower alkyl, amino-lower alkyl, mono-lower alkylamino-lower alkyl, di-lower alkylamino-lower alkyl and the group —CH$_2$R$_6$, R$_6$ being defined as above and pharmaceutically acceptable acid addition salts thereof.

In a further preferred aspect of the present invention, $R_1$ signifies hydrogen and $R_5$ signifies hydrogen, lower alkyl, or lower alkenyl.

Most preferred of the compounds of formula II are:

2,3,4,5-tetrahydro-7,8-methylenedioxy-1H-3-benzazepine;

2,3,4,5-tetrahydro-3-methyl-7,8-methylenedioxy-1H-3-benzazepine;

3-ethyl-2,3,4,5-tetrahydro-7,8-methylenedioxy-1H-3-benzazepine; and 3-allyl-2,3,4,5-tetrahydro-7,8-methylenedioxy-1H-3-benzazepine.

Compounds of formula I above wherein B signifies a —CH$_2$— group, including the novel 3-benzazepines of formula II, form pharmaceutically acceptable acid addition salts with pharmaceutically acceptable organic or inorganic acids. Suitable acids for this purpose including hydrochloric acid, phosphoric acid, hydrobromic acid, citric acid, sulfuric acid, succinic acid, maleic acid, p-toluene-sulfonic acid, tartaric acid, and the like.

The compounds of formula I above and the preferred novel 3-benzazepines of formula II above can be prepared following a variety of synthetic routes, including the novel process aspect which forms a part of the present invention.

In following the aforementioned novel process aspect of this invention, the compounds of formula I above may be prepared by the chloromethylation of a compound of the formula

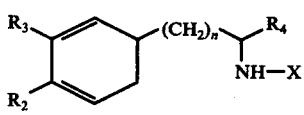  III wherein $R_2$–$R_4$ and $n$ are as described above and X is any suitable protecting group, preferably acyl or phthaloyl, provided that if X is phthaloyl, there is no hydrogen on the nitrogen.

This chloromethylation results in the preparation of a compound of the formula

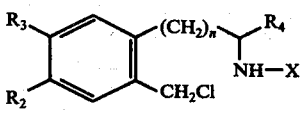  IV wherein $R_2$–$R_4$, X and $n$ are as described above.

The chloromethylation is carried out using special reaction conditions which effect the introduction of the —CH$_2$Cl group directly into the aromatic compound of formula III via the interaction of said formula III compound with formaldehyde and hydrogen chloride. The chloromethylation reaction is expediently effected in the presence of an inert organic solvent such as a halogenated hydrocarbon, for example, ethylene chloride, tetrachloroethane and the like, or acetic acid. It should be noted that the starting materials of formula III above bear substituents on the aromatic portion of the molecule which direct the incoming chloromethyl group to the position ortho to the acylamido-lower alkyl side chain.

The chloromethylated compound of formula IV above is then converted to the corresponding cyanomethylated compound of the formula

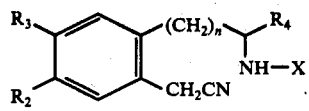  V wherein $R_2$–$R_4$, X and $n$ are as described above.

The conversion of the chloromethyl group of the compounds of formula IV to the cyanomethyl group of the compounds of formula V can be accomplished, for example, by treating the compounds of formula IV with an alkali metal cyanide, preferably sodium or potassium cyanide. The conversion of the compounds of formula IV above to the compounds of formula V is expediently effected in the presence of an aprotic polar solvent such as dimethylsulfoxide (DMSO), N,N-dimethylformamide (DMF) and the like, with DMSO being preferred.

The so-obtained cyanomethyl compound of formula V is then converted to the corresponding ethyl ester compound of the formula

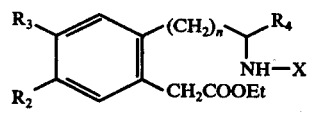  VI wherein $R_2$–$R_4$, X and $n$ are as described above.

The conversion of the compound of formula V above to the corresponding ester compound of formula VI can be accomplished following standard techniques, such as, by alcoholyzing the nitrile of formula V. Alcoholysis of the nitrile can be effected by refluxing the nitrile in absolute alcohol and anhydrous acid, preferably hydrochloric acid, to obtain the imido ester salt, with subsequent addition of water to obtain the ester. This alcoholysis can also be accomplished by dissolving the cyanomethyl derivative in a mineral acid saturated ethanol solution. Suitable mineral acids used in preparing the saturated alcohol solution are hydro-halic acids such as hydrogen chloride and hydrogen bromide or sulfuric acid.

The so-obtained ester compound of formula VI is then hydrolyzed to the corresponding acetic acid compound of the formula

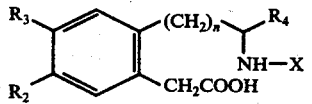  VII wherein $R_2$–$R_4$, X and $n$ are as described above.

The hydrolysis of the ester compound of formula VI to the corresponding acid of formula VII may be accomplished, for example, by treating the ester in an aqueous solution containing either acidic or basic catalysts. Suitable acid catalysts for this purpose include hydrochloric acid, sulfuric acid and the like while suitable basic catalysts include alkali and alkaline earth metal hydroxides such as sodium hydroxide, potassium hydroxide, calcium hydroxide and the like.

The nitrogen protecting group present in the so-obtained acetic acid compound of formula VII above is then split off to yield the corresponding amino acid compound of the formula

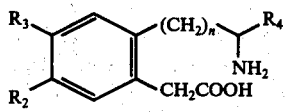

VIII wherein $R_2$–$R_4$ and n are as described above.

The splitting off of the protecting group may be accomplished using conventional techniques. Thus, for example, if the protecting group utilized is an acyl group, the desired amino acid compound of formula VIII can be obtained by de-acylation of the formula VII compound. This de-acylation can be effected by heating the formula VII compound in an acid or alkaline solution. Suitable acids for this purpose include hydrochloric acid, sulfuric acid and the like, suitable bases include sodium and potassium hydroxide. Likewise, if the protecting group utilized is a phthaloyl group, this can be split off by alkaline treatment of the formula VII compound, preferably with sodium hydroxide, or by hydrazinolysis, preferably with hydrazine hydrate.

In the next step of this process, the amino acid compound of formula VIII above is condensed to the corresponding compound of formula I wherein B signifies —CO—. The lactam thus obtained can be represented by the following formula

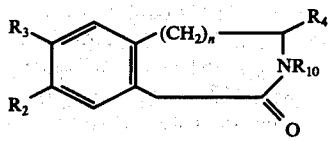

Ia wherein $R_2$–$R_4$ and $n$ are as described above and $R_{10}$ signifies hydrogen, benzyl, or lower alkyl.

The conversion of the amino acid compound of formula VIII above to the corresponding lactam of formula Ia may be accomplished following a variety of procedures. For example, thermal treatment of the compound of formula VIII will effect condensation of said compound to the desired lactam. This thermal condensation is expediently effected using temperatures above room temperature, and is most preferably effected at the reflux temperature of the reaction medium. It is expedient to conduct the thermal condensation in the presence of a high boiling point solvent which is capable of forming an azeotropic mixture with water. Suitable solvents for this purpose include tetralin, xylene and the like. In cases where the lactam is formed via thermal condensation, it is preferable to first form the secondary amine derivative of the compound of formula VIII since condensation occurs more readily using said compound. The benzyl derivative, which can be represented by the formula

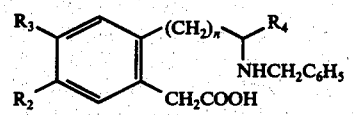

VIIIa wherein $R_2$–$R_4$ and $n$ are as described above may be prepared, for example, by treating the amino acid derivative of formula VIII with benzaldehyde in the presence of sodium borohydride. If the benzyl derivative of formula VIIIa above is utilized, the lactam obtained upon thermal condensation will bear a benzyl group substituted on the nitrogen atom.

Alternately, conversion of the amino acid compound of formula VIII to the lactam of formula Ia wherein $R_{10}$ is hydrogen can be accomplished by treating a solution of the amino acid compound with a condensing agent such as 1-cyclohexyl-3-(2-morpholinoethyl)carbodiimide methotoluenesulfonate to yield the desired lactam. Temperature is not critical to this process aspect and for the sake of convenience the condensation is expediently effected at room temperature.

The lactam of formula Ia above is then reduced to the corresponding compound of formula I wherein B signifies —$CH_2$—, i.e. to a compound of the formula

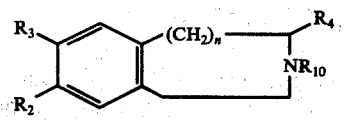

Ib wherein $R_2$–$R_4$, $R_{10}$ and $n$ are as described above. The reduction of the lactam of formula Ia to the corresponding compound of formula Ib can be accomplished using conventional reduction techniques. For example, the carbonyl group can be reduced to the desired methylene group by treating a compound of formula Ia above with a suitable reducing agent such as lithium aluminum hydride, lithium borohydride, borane and the like.

If desired, the compound of formula Ib wherein $R_{10}$ signifies benzyl can be debenzylated using standard catalytic dehydrogenation techniques. Substituents can be introduced onto the nitrogen atom in the heterocyclic ring system after reduction and debenzylation of the formula Ia compound. This substitution of the nitrogen atom can be accomplished following a variety of procedures, depending upon the nature of the group being introduced. Thus, for example, a lower alkyl or substituted lower alkyl group can be introduced using standard alkylation procedures while an acyl or substituted acyl group can be introduced using standard acylation techniques. Additional details as to the introduction of substituents on the heterocyclic ring system are presented hereinbelow.

The compounds of formula III above used as starting materials in the above described process are known or can be prepared in analogy to the preparation of the known compounds.

In addition to the novel process aspect described above, the 2,3,4,5-tetrahydro-1H-3-benzazepines of formula II above wherein $R_5$ signifies hydrogen can be prepared by the catalytic hydrogenation of a compound of the formula

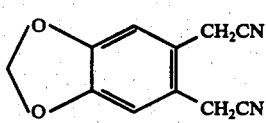

IX in the presence of ammonia using a nickel catalyst such as Raney nickel. The catalytic hydrogenation of the compound of formula IX results in the formation of the benzazepine of the formula

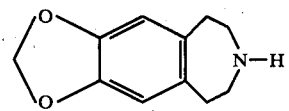

This hydrogenation procedure is preferably effected in the presence of an inert organic solvent such as methanol, ethanol and the like.

The 3-acetyl derivative can be prepared by acetylation of the compound of formula IIc. This acetylation produces the compound of the formula

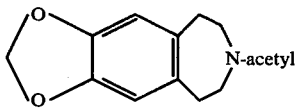

The compounds of formula II above wherein $R_1$ signifies halogen can be prepared by halogenation of the compound of formula IId, for example by bromination with bromine in acetic acid or by chlorination with chlorine.

The compounds of formula II above wherein $R_5$ signifies a lower alkyl, a lower alkenyl, or a substituted lower alkyl group such as a di-lower alkyl-amino-lower alkyl group can be prepared by the alkylation of the compound of formula IIc above. This alkylation is preferably accomplished by first forming the N-sodio derivative of the compound of IIc and then treating this N-sodio derivative with an alkylating agent such as an alkyl halide, alkyl sulfate, alkenyl halide, and the like. The N-sodio derivative of IIc can be prepared by heating the formula IIc compound with sodium hydride.

The compounds of formula II above wherein $R_5$ signifies carbalkoxy-lower alkyl can be prepared by reacting the N-sodio derivative of the compound of formula IIc with a compound of the formula

wherein m is an integer from 1–7.

The reaction between the N-sodio derivative of IIc and a compound of formula X is expediently effected in the presence of an inert organic solvent such as dimethylformamide.

The compounds of formula II above wherein $R_5$ signifies carboxy-lower alkyl can be prepared by hydrolysis of the corresponding ester derivative, i.e., the corresponding compound wherein $R_5$ signifies carbalkoxy-lower alkyl. The hydrolysis can be effected by treating the ester derivative with a solution of an alkali metal hydroxide, preferably sodium hydroxide, in water. The reaction is expediently effected in the presence of an inert organic solvent such as methanol, ethanol and the like.

The compounds of formula IIb above may be prepared by reacting the compound of formula IIc above with a compound of the formula

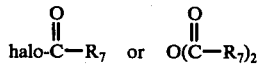

wherein $R_7$ is as described above.

The reaction of the compound of formula IIc with a compound of formula XI is expediently effected in the presence of an inert organic solvent such as an aromatic hydrocarbon, for example, benzene, toluene and the like.

The compounds of formula I above and their pharmaceutically acceptable acid addition salts exhibit analgesic, appetite suppressant and anti-edema activity. Their useful analgesic activity is shown in warm-blooded animals utilizing for example a test which is a modification of that described by Eddy (1950), Wolfe and MacDonald (1944) and Eddy and Leimbach (1952). The method determines the reaction time of mice dropped onto a hot plate maintained at 55° ± 0.5° C. Six groups of male mice (5 mice/group) weighing between 20–30 grams are utilized. The initial reaction time of these mice is determined once, and the reaction time of each group is then averaged. The mice are then administered the vehicle and/or the compound to be tested by the oral, intraperitoneal or subcutaneous route. The average reaction time of each group is determined again at 30, 60 and 90 minutes after compound administration and is compared to controls. Reaction time is recorded as percent changes from control. All groups are averaged before and after treatment. A combined reaction time average (recorded as percent change of reaction time threshold from controls) for all three periods is plotted against dose on graph paper, and a curve is drawn. The $ED_{50}$ is read from this curve.

Utilizing this standard procedure, compounds such as 1,2,3,4,5,6-hexahydro-8,9-methylenedioxy-3-benzazocine (Compound A), 2,3,4,5-tetrahydro-7,8-dimethyl-1H-3-benzazepine (Compound B) and 7,8-methylenedioxy-2,3,4,5,-tetrahydro-1H-3-benzazepine (Compound C) show an $ED_{50}$ of 200 mg., of 6 mg., and 200 mg. respectively.

The appetite suppressant activity of the compounds of formula I is demonstrated in warm-blooded animals utilizing a standard anti-obesity test. In this test, six groups of 5 female rats each are weighed and starved for 24 hours. The animals are arranged so that each group has the same total weight. A dose of the test compound in distilled water is administered subcutaneously, the body weight recorded and a known weight of food pellets given. After 4 hours, the animals and food are weighed, and the weight gained and food eaten are determined. The results are expressed as the dose which reduces appetite by 50 percent ($A.R._{50}$) for weight gained, food eaten, and water intake. Utilizing this standard procedure, compounds A, B and C above show an $A.R._{50}$ as follows:

| Compound | DOSE, $A.R._{50}$ | | |
|---|---|---|---|
| | Food Eaten | Weight Gained | Water Drunk |
| Compound A | 27 mg. | 20 mg. | 33 mg. |
| Compound B | 1 mg. | 1 mg. | 1 mg. |
| Compound C | 8 mg. | 6 mg. | — |

The anti-edema activity of the compounds of formula I is demonstrated in warm-blooded animals utilizing a standard anti-edema test. In this test, sixty male albino rats are given 10 ml. per kilogram of body weight of vehicle containing, for the treatment groups, the test compound. Water is given to bring the total volume to 5 ml. in each animal. One hour later 0.05 ml. of a 1 percent type No. 7 carrageenan in normal solution is injected into the right hind paw of the rat. The paw volume is measured immediately after the injection of the phlogistic agent and again 3 hours later. The difference is recorded as volume of edema and the dose required to produce a 30 per cent reduction in edema is estimated. Utilizing this standard procedure, compounds A, B and C above show an $ED_{30}$ of 78 mg., 3.6 mg., and 12 mg. respectively.

The compounds of formula I can be used together with conventional pharmaceutical carriers suitable for parenteral or enteral administration such as, for example water, gelatin, starch, magnesium stearate, petroleum jelly and the like. They can be administered in conventional pharmaceutical forms, for example, solid forms such as capsules, tablets, or liquid forms such as solutions or emulsions. Moreover, the pharmaceutical compositions containing compounds of formula I can be subjected to conventional pharmaceutical expedients such as sterilization, and can contain conventional pharmaceutical excipients such as preservatives, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of the aforesaid compounds of formula I; with a dosage range of from about 1 mg to about 100 mg being the preferred oral administration and a dosage range of from about 1 mg to about 50 mg being preferred for parenteral administration. However, for any particular subject, the specific dosage regimen should be adjusted according to individual need. It is to be understood that the dosages set forth herein are exemplary only and that they do not, to any extent, limit the scope or practice of this invention.

The following examples further illustrate the invention. All temperatures are in degrees centigrade unless otherwise indicated.

EXAMPLE 1

Preparation of N-(6-Chloromethyl-3,4-methylenedioxyphenethyl) acetamide

In a 100 ml round-bottom flask provided with a stirrer, thermometer, gas inlet tube, and a condenser were placed 4.12 g of N-acetyl-homopiperonylamine (0.02 mole), 2.1 g of 37% formaldehyde solution, and 50 ml of ethylene chloride. The mixture was cooled to 3° and hydrogen chloride passed into the stirred mixture. After about 15 minutes a thick paste of crystals had formed. At this point, another 2.1 g of 37% formaldehyde was added and the mixture allowed to stir until all the solid had dissolved. The solution was then poured into ice water and the lower ethylene chloride layer separated, washed three times with water, then dried. The clear ethylene chloride solution was freed of solvent in the rotary evaporator, leaving the above-named product as a crystalline solid. After recrystallization from acetone, the solid melted at 116.5°–122°.

EXAMPLE 2

Preparation of N-(6-Cyanomethyl-3,4-methylenedioxyphenethyl) acetamide 4.7 g of N-(6-chloromethyl-3,4-methylenedioxyphenethyl) acetamide was dissolved in 10 ml of DMSO and 1.32 g (0.028 mole) of sodium cyanide added to the stirred solution. Within a few minutes, the temperature rose from 25° to 32° C. After 1.5 hrs at ambient temperature the mixture was poured into ice and water. The suspension was extracted with three 50-ml portions of benzene. The benzene layers were washed with saturated brine six times, then with water, the solution dried, and the solvent distilled in the rotary evaporator leaving the above-named product as a crystalline solid, m.p. 153.3–155.5.

EXAMPLE 3

Preparation of Ethyl ester of 6-(2-acetamidoethyl)-3,4-methylenedioxyphenyl-acetic acid 2.58 g (0.0104 moles) of N-(6-cyanomethyl-3,4-methylenedioxyphenethyl) acetamide was dissolved in 30 ml of ethanol saturated with hydrogen chloride. After six hrs at 25°, the mixture was poured into ice and water. The ester was collected by extraction with benzene (3 × 25 ml), the benzene extracts washed successively with water, saturated bicarbonate solution, and water, then dried. Distillation of the solvent gave a mass of long prismatic needles. These were recrystallized once from a mixture of ethanol and petroleum ether (b.p. 60°–90°) to yield the above-named product, m.p. 123°–125°.

EXAMPLE 4

Preparation of 6-(2-Acetamidoethyl)-3,4-methylenedioxyphenylacetic acid

A small sample of the ethyl ester prepared in Example 3 was warmed on the steam bath in alcoholic solution with excess sodium hydroxide. The solution was brought to pH 9, a flocculent precipitate filtered off, and the clear filtrate acidified to pH3. After standing overnight, clusters of crystals had separated. The crystals were recovered by filtration, washed with a little cold water, then recrystallized from a minimum of hot water to yield the above-named product, m.p. 188–190.5.

EXAMPLE 5

Preparation of 6-(2-Aminoethyl-3,4-methylenedioxyphenylacetic acid hydrochloride One g of the acetamido derivative prepared in Example 4 was refluxed with 20 ml of 4N HCl for 10 hrs. The excess acid was removed on the rotary evaporator leaving a solid residue which was recrystallized from a mixture of isopropanol and ethyl acetate to yield white crystals of the above-named product, m.p. 210°–212°.

EXAMPLE 6

Preparation of 6-(2-Benzylaminoethyl-3,4-methylenedioxyphenylacetic acid

To a solution of 26 g of the amino acid hydrochloride prepared in Example 5 (0.1 mole), in 80 ml of water, was added 8.4 g of sodium hydroxide (0.21 moles), in 42 ml of water, followed by 11.7 g (0.11 moles) of benzaldehyde. The initially turbid mixture immediately cleared. After one hour, the mixture was evaporated to a thick syrup on the rotary evaporator, the syrup dissolved in 75 ml of ethanol, and the evaporation to syrup repeated. The residue was dissolved in 500 ml of methanol and 6.5 g of sodium borohydride (0.17 moles) added in several portions. After stirring for 1.5 hours, the solvent was removed on the rotary evaporator, leaving a grayish solid. This residue was dissolved in 200 ml of water and 10 percent hydrochloric acid added to pH 7. The precipitate which formed was collected by filtration, washed with water, and dried to yield the above-named product, m.p. 217°–218° dec.

EXAMPLE 7

Preparation of The Lactone 24.7 g of the amino acid prepared in Example 6 was refluxed with 500 ml of xylene under a Dean-Stark trap for seven hours. During this period, water was steadily collected and the solid gradually dissolved. The clear solution was distilled in the rotary evaporator leaving a crystalline residue, m.p. 141°–142°. This was recrystallized from isopropanol to yield off-white crystals of 3-benzyl-7,8-methylenedioxy-1,3,4,5-tetrahydro-2H-3-benzazepin-2-one, m.p. 141°–142°.

Similarly, 0.005 moles (1.3 grams) of 6-(2-aminoethyl)-4,5-methylenedioxy phenyl-acetic acid hydrochloride were dissolved in 15 ml of water and to this solution was added 2.12 grams of 1-cyclohexyl-3-(2-morpholinoethyl)carbodiimide methotoluenesulfonate in 20 ml of water. After 2 hours at room temperature the precipitate that had formed was filtered off, washed and dried to yield 1,3,4,5-tetrahydro-7,8-methylenedioxy-2H-3-benzazepin-2-one, m.p. 236°–237°. After recrystallization from ether the product melted at 238°–239°.

EXAMPLE 8

Preparation of dl-1-(3,4-Dimethyl-6-chlormethylphenyl)-2-acetamidopropane 4.1 g of rac. 1-(3,4-dimethylphenyl)-2-acetamidopropane was dissolved in 40 ml of 1,1,2,2-tetrachlorethane in a 100-ml RB flask provided with a stirrer, thermometer, condenser, and gas inlet tube. Twelve ml of 37% formaldehyde was added, and a stream of hydrogen chloride passed into the stirred mixture as the temperature rose to 50°, where it was maintained for 5 hrs. At this point, the mixture remained overnight at room temperature. The reaction mixture was poured into water, the organic phase was washed twice with water, dried, and the solvent distilled in the rotary evaporator, leaving 4.2 g of a colorless oil. The oil was refluxed with four 100-ml-portions of petroleum ether (b.p. 60-0-°), and from the combined extracts, a mass of cottony needles separated. The solid was collected by filtration and freed of solvent in vacuo to yield the above-named product, m.p. 72°–73°.

EXAMPLE 9

Preparation of dl-1-(3,4-Dimethyl-6-cyanomethylphenyl)-2-acetamidopropane

Two g of the chloromethyl compound (0.0079 moles) prepared in Example 8 was dissolved in 20 ml of DMSO and 0.77 g (0.0119 moles) of KCN added. The suspension was stirred and gradually warmed to 45° over a period of 45 minutes, at which point the temperature suddenly rose to 54°, where it remained for some 5–7 minutes and then began to fall. After another 15 minutes, the reaction mixture was poured into ice water, the oil collected by three extractions with ether-benzene (50 ml each of a 1:1 mixture), the combined extracts washed with saturated brine, dried over MgSO$_4$, and the solvents distilled in the rotary evaporator. A white crystalline solid remained which was slurried in a mixture of ethyl acetate and petroleum ether (b.p. 60°–90°), leaving the above-named product as a solid, m.p. 140°–141°.

EXAMPLE 10

Preparation of dl-6-(2-Acetamidopropyl)-3,4-dimethylphenylacetic acid 7.1 g of the nitrile (0.03 mole) prepared in Example 9 and 75 ml of ethanol saturated with hydrogen chloride was stirred for one hour at room temperature, then refluxed for four hours. The cooled solution was poured into 500 ml of ice water and the aqueous solution extracted four times with 50-ml portions of chloroform. The combined chloroform extracts were washed with water, dried (MgSO$_{b4}$), then distilled in the rotary evaporator to yield the ethyl ester of the above-named product as a pale yellowish oil.

This crude ethyl ester was refluxed with 25 ml of 10% sodium hydroxide and 25 ml of ethanol for one hour, then the ethanol distilled. The residue was cooled and the undissolved material removed by three washes with benzene (25 ml each). The aqueous residue was then acidified to pH 3 and extracted three times with 50-ml-portions of chloroform. These extracts were washed with water, dried (MgSO$_4$), distilled in the rotary evaporator, to yield an oil which crystallized on standing overnight. A sample of this material was recrystallized from ethyl acetate and petroleum ether (b.p. 60°–90°) to yield the above-named product as white crystals m.p. 67°–69°.

EXAMPLE 11

Preparation of dl-6-(2-Aminopropyl)-3,4-dimethylphenylacetic acid 0.5 g of the acetamido acid prepared in Example 10 was refluxed for 18 hours with 20 ml of 6N hydrochloric acid. The excess acid was removed in the rotary evaporator, leaving a semi-solid residue. This was dissolved in five ml of water and sodium bicarbonate solution added to pH 6–7, whereupon a voluminous white precipitate formed. After chilling for an hour, the solid was recovered by filtration and recrystallized from aqueous ethanol. The white crystals of the above-named product thus obtained melted at 222.5°–223° with decomposition.

EXAMPLE 12

Preparation of dl-4,7,8-Trimethyl-1,3,4,5-tetrahydro-2H-3-benzazepin-2-one 3.6 g of the amino acid prepared in Example 11 was refluxed in 36 ml of tetralin under a Dean-Stark trap for 24 hours, after which the solid had dissolved. The cooled solution was diluted with 150 ml of petroleum ether (b.p. 60°–90°) and cooled for an hour, the crystals that separated were recovered by filtration and washed with petroleum ether. The above-named product was recrystallized from ethanol, m.p. 226°–227°.

EXAMPLE 13

Preparation of dl-2,7,8-Trimethyl-2,3,4,5-tetrahydro-1H-3-benzazepine hydrochloride A slurry of 3.7 g of the lactam (0.0182 moles) prepared in Example 12 in 20 ml of tetrahydrofuran was cooled to 0° and 40 ml of a 1M solution of borane in tetrahydrofuran gradually added. After five minutes at 0°–5°, almost all of the lactam had dissolved, whereupon the mixture was heated to boiling. The clear refluxing solution deposited some gelatinous material at the liquid-vapor interface after about fifteen minutes. Refluxing was continued for another three hours, then the mixture was cooled in an ice bath and the excess borane cautiously decomposed by the dropwise addition of 50 ml of 10 percent hydrochloric acid. The mixture was warmed on the steam bath to boil off the tetrahydrofuran and the cooled residual solution extracted with several portions of benzene to remove any nonbasic material. After alkalizing to pH 11, the base was extracted with three 50-ml portions of benzene and one 50-ml portion of ether. The combined extracts were washed with water, dried ($K_2CO_3$), and the solvent distilled in the rotary evaporator. The base was then dissolved in 25 ml of ether and an excess of ethereal hydrogen chloride added. The solvent and excess acid were distilled in vacuo and the syrupy residue crystallized when rubbed under ethyl acetate. This crystalline hydrochloride, of the above named product melted at 219.5°–221°. It was recrystallized from a mixture of ethyl acetate and isopropanol and formed white crystals, m.p. 218°–219°.

EXAMPLE 14

In analogy to the procedures described in Example 13, there may be prepared 7,8-methylenedioxy-2,3,4,5-tetrahydro-1H-3-benzazepine, m.p. 82°–84°, using the lactam described in paragraph 2 of Example 7.

EXAMPLE 15

Preparation of
dl-1-(3,4-Methylenedioxy-6-chloromethylphenyl)-2-acetamido-propane A mixture of 2.21 g of N-acetyl-α-methylhomopiperonylamine (0.01 moles), 6.1 ml of 37 percent formaldehyde (0.15 moles) and 20 ml of ethylene chloride was stirred at 0°–3° while a stream of hydrogen chloride was passed in. After 25 minutes, the suspension was filled with a mass of white crystals that was filtered off and washed with ethylene chloride. The solid was slurried with several portions of hot acetone to yield the hydrochloride of the above-named product as a white solid, m.p. 163.5°–164.5.

The hydrochloride-free amide, or free base, can be prepared as follows: Alternately the crystalline mass obtained by filtration of the chloromethylation mixture was resuspended in ethylene chloride and sufficient sodium bicarbonate solution added to neutralize the acidity; two homogeneous phases resulted. The organic layer was washed with water, then dried, and the solvent removed leaving a solid residue. This was recrystallized from isopropanol yielding a crystalline solid, mp 132°–133°; which is the HCl-free amide, i.e. the "free base" named above.

The starting material was prepared by refluxing α-methylhomopiperonyl amine with acetic anhydride in toluene for 4.5 hours followed by distillation of the reaction mixture, N-acetyl-α-methylhomopiperonylamine distilled at 138°–142°/0.2 mm as a colorless viscous oil that set to a mass of white crystals when rubbed under petroleum ether (b.p. 60°–90°). M.p. 94°–95° after recrystallization from petroleum ether-ethyl acetate.

EXAMPLE 16

Preparation of
dl-N-(6-Cyanomethyl-α-methyl-3,4-methylenedioxyphenethyl)acetamide 26.5 g of the amide hydrochloride, (0.087 moles) prepared in Example 15 was added to 265 ml of DMSO and 25.6 of sodium cyanide (0.52 moles). The temperature rose from 24° to 40°, where it was maintained for three hours. The suspension was poured into 1500 ml of ice water and the resulting mixture extracted three times with 500 ml portions of chloroform. The combined extracts were washed with saturated brine, then water, dried ($MgSO_4$), and distilled on the rotary evaporator, leaving 20 g of a solid. This solid was first slurried in a 1:1 mixture of ethyl acetate and petroleum ether (b.p. 60°–90°) and then recrystallized from 200 ml of toluene. After chilling, there was obtained the above-named product in crystalline form, m.p. 134°–135.5°.

EXAMPLE 17

Preparation of
dl-6-(2-Acetamidopropyl)-1,3-benzodioxole-5-acetic acid

A mixture of 202 ml of ethanol saturated with hydrogen chloride and 20.2 g (0.078 moles) of the nitrile prepared in Example 16 was stirred at room temperature, then refluxed for 4.5 hours. The ammonium chloride was removed by filtration and the solvent removed from the filtrate in the rotary evaporator. The syrupy yellow residue was then refluxed with a solution of 18.8 g of sodium hydroxide (0.408 moles) in 468 ml of 50 percent aqueous ethanol for 48 hours. After distilling the bulk of the ethanol, the residual solution was acidified to pH 3, whereupon the crystalline acid separated. The solid was collected by filtration, washed and dried, m.p. 195°–197°. Recrystallization from aqueous ethanol gave crystals of the above-named product, m.p. 197°–198°.

The hydrolytic mother liquor also contained the deacetylated amino acid which precipitated when the pH of the filtrate was adjusted to 7 and the solution chilled.

EXAMPLE 18

Preparation of
dl-4-Methyl-7,8-methylenedioxy-1,3,4,5-tetrahydro-2H-3-benzazepin-2-one The amino acid together with the residue that remained on evaporating to dryness the mother liquor described in Example 17 were refluxed in 450 ml of tetralin under a Dean-Stark trap for 45 minutes and the hot solution filtered from insoluble material. On cooling, the filtrate deposited crystals. An equal volume of petroleum ether (b.p. 30°–60°) was added to complete the crystallization. On filtration, a creamy white crystalline product was collected. It was washed well with petroleum ether and dried, m.p. 177°–178°. Recrystallization from ethyl acetate gave the above-named product as white cottony needles, m.p. 175°–175.5°.

EXAMPLE 19

Preparation of
dl-2-Methyl-7,8-methylenedioxy-2,3,4,5-tetrahydro-1H-3-benzazepine hydrochloride The cyclic lactam obtained in Example 18 (4.4 g, 0.002 moles) in 60 ml. of tetrahydrofuran was treated with 60 ml. of 1M borane in tetrahydrofuran at 0°. The solid dissolved and the mixture was refluxed for three hours after which 100 ml of 3N hydrochloric acid was added cautiously and the solution heated on the steam bath until the tetrahydrofuran had distilled. The cooled solution was extracted twice with 50 ml portions of chloroform to remove unreacted lactam, the aqueous layer then made alkaline, and the base collected by three 50 ml extractions with 1—1 benzene-ether. The extract was washed with water, dried ($K_2CO_3$), and the solvent distilled, leaving 3.0 g. of a very pale amber oil. This was dissolved in a mixture of isopropanol-ether and an excess of ethereal hydrogen chloride added. The resulting creamy white solid was collected, washed and dried, m.p. 266°–268° (dec.). Upon recrystallization from water, the crystalline hydrochloride of the above-named product was obtained, m.p. 271.5°–272.5° (dec.).

EXAMPLE 20

Chloromethylation of N-Acetylhomoveratrylamine 44.6 g (0.2 mole) of N-acetylhomoveratrylamine, 124 ml of 37 percent formaldehyde, and 400 ml of chloroform were mixed and cooled to −15°. Hydrogen chloride was passed into the stirred suspension at −15°. As the mixture became saturated with HCl crystals began to form and suddenly after about 1.7 hours the reaction vessel was filled with a mass of crystals. The crystals were transferred to a sintered glass funnel and as much liquid as possible removed by suction; the filter cake was washed twice with chloroform and then transferred to a vacuum dessicator, (20 mm, $CaCl_2$ and NaOH flakes were it was brought to constant weight, 50 g, m.p. 139°–143°.

A sample of this material was recrystallized from ethyl acetate and obtained as clusters of sword-shaped crystals, m.p. 151°–153° dec with evolution of HCl. This substance is the hydrochloride of N-(6-chloromethyl-3,4-dimethoxyphenethyl)acetamide.

EXAMPLE 21

Preparation of 6-(2-Acetamidoethyl)-4,5-dimethoxyphenylacetonitrile 50 g of the chloromethylated product obtained in Example 20, as the hydrochloride, was added to a stirred suspension of 20 g of sodium cyanide in 500 ml of dimethylsulfoxide. The temperature of the stirred mixture spontaneously rose to 44° during the course of 30 minutes and then began to fall. After 1 hr. the mixture was poured into 1.5 l of ice water and extracted five times with 200-ml portions of chloroform. The chloroform extracts were washed four times with saturated brine, dried ($MgSO_4$), and finally distilled in the rotary evaporator, leaving a cream-colored solid, m.p. 134°–136°. Recrystallization of this solid from ethyl acetate gave crystals of the above-named product, m.p. 138°–140°.

EXAMPLE 22

Preparation of 2-(2-Benzylaminoethyl)-4,5-dimethoxyphenylacetic acid 10.0 g of the nitrile obtained in Example 21 was stirred for one hour with 150 ml of ethanol saturated with hydrogen chloride, then refluxed for four hours. When cool, the ammonium chloride was removed by filtration and the solvents distilled from the filtrate leaving 11.7 g of a pale amber oil. The oil was not characterized but refluxed with 8.64 g of sodium hydroxide and 180 ml of 50% aqueous ethanol for 48 hours. This solution was evaporated to dryness in the rotary evaporator, then dissolved in 36 ml of water and the pH adjusted to 7.0. To this solution, 1.6 g of sodium hydroxide (0.04 moles) in 8 ml of water was added, followed by 4.24 of benzaldehyde (0.04 moles). After stirring for 15 minutes, the solution was distilled to a semi-solid in the rotary evaporator. Fifty ml of isopropanol was added to the residue and the process repeated. The residue was dissolved in 200 ml of methanol, 2.3 ml of sodium borohydride (0.060 moles) added in several portions, then the mixture stirred for 0.5 hour. The methanol was distilled in the rotary evaporator, 60 ml of water added to the residue and the pH adjusted to 7.5 by the addition of 10 percent hydrochloric acid. After chilling in ice for 0.5 hour, the white precipitate that had formed was collected, m.p. 208°–210° (turbid). Recrystallization from aqueous ethanol gave the above-named product m.p. 213°–213.5°.

EXAMPLE 23

Preparation of 3-Benzyl-7,8-dimethoxy-1,3,4,5-tetrahydro-2H-3-benzazepin-2-one

A stirred suspension of 4.1 suspension of 4.1 g of the benzylamino acid obtained in Example 22 was refluxed in 75 ml. of xylene under a Dean-Stark trap for 24 hours, at the end of which time a clear solution had resulted. Distillation of the xylene in vacuo left the above-named product as shining white plates, m.p. 141°–142°. A sample of the cyclic lactam recrystallized from toluene melted at 141°–142°.

EXAMPLE 24

Preparation of 4,5-Methylenedioxy-1,2-bis(chloromethyl)benzene

The above-named product was prepared following the procedures of F. Dallacker, K. W. Glombitza and M. Lipp, Liebig's Ann., 643, 67–82 (1961).

EXAMPLE 25

Preparation of 4,5-Methylenedioxy-1,2-benzenediacetonitrile

To a stirred suspension of 98 g (2.0 moles) of sodium cyanide in 1.75 l. of dimethylsulfoxide, cooled to 18°–20°, 175 g (0.8 moles) of 4,5-methylenedioxy-1,2-bis(chloromethyl)benzene was added in 1 portion. The temperature rose rapidly, but was arrested and maintained at 40° by intermittent cooling until it fell spontaneously - about 20–30 minutes. The reaction mixture was poured into 3 l. of ice-water and 1 l. of chloroform. When the ice had melted, the organic layer was separated and the aqueous layer extracted twice more with 500 ml portions of chloroform. The combined extracts were washed five times with saturated salt solution (500 ml each), once with water, and dried over magnesium sulfate. Distillation of the solvent at reduced pressure in the rotary evaporator gave a pale yellow crystalline residue. This solid was recrystallized from approximately 2 l. of isopropanol and yielded the above-named product as a cream colored solid, m.p. 105°–107°.

EXAMPLE 26

Preparation of 2,3,4,5-Tetrahydro-7,8-methylenedioxy-1H-3-benzazepine 119 g. (0.595 moles) of 4,5-methylenedioxy-1,2-benzenediacetonitrile was hydrogenated in 2.4 l. of ammonia-saturated ethanol at an initial pressure of 1,000 PSI and 100° C in the presence of 24 g of Raney nickel for 4 to 5 hours. The cooled autoclave contents were filtered to remove the nickel, the catalyst washed with 500 ml of hot ethanol, and the filtrate distilled at reduced pressure, leaving 120 g of dark gray oil. This oil was distilled in vacuo using a Claisen still head and several fractions were collected. The low boiling fractions contained the desired produ ct which upon purification yielded the above-named product, m.p. 82°-84°.

EXAMPLE 27

Preparation of 6-Bromo-2,3,4,5-tetrahydro-7,8-methylenedioxy-1H-3-benzazepine hydrochloride 11.65 g of 3-acetyl-2,3,4,5-tetrahydro-7,8-methylenedioxy-1H-3-benzazepine was dissolved in 200 ml of acetic acid and to the stirred solution at 55°, a solution of 8.3 (0.053 moles) of bromine in 75 ml of acetic acid was added during the course of an hour. When about two-thirds of the bromine had been added, a coarse yellow-orange precipitate began to form. This mixture was stirred for three hours after which time the test for free bromine (starch-potassium iodide paper) was weak, whereupon the reaction mixture was poured into a liter of cold water and allowed to stand overnight. The precipitate that had formed was recovered by filtration, washed with water and dried, m.p. 137°-139°. A small sample was recrystallized from aqueous ethanol to yield the above-named product as white crystals, m.p. 133°-137°.

EXAMPLE 28

Preparation of 2,3,4,5-Tetrahydro-3-methyl-7,8-methylenedioxy-1H-3-benzazepine 19.1 g (0.1 M) of 2,3,4,5-tetrahydro-7,8-methylenedioxy-1H-3-benzazepine base was dissolved in 100 ml of methanol and 12 ml of 37% formaldehyde (0.148 moles) added thereto. In a few minutes, a new precipitate began to form with the evolution of heat. To this suspension 5 g of methanol-washed Raney nickel was added and the mixture shaken under 50 lbs. of hydrogen pressure. Uptake of hydrogen was complete in about an hour after which the excess hydrogen was vented, the catalyst removed by filtration, washed and the combined filtrates freed of solvent in the rotary evaporator. To remove the excess formaldehyde, the residue was dissolved in 100 ml of benzene, the solution washed four times with water, then dried, and the solvent distilled leaving a syrup. This was distilled from a small Claisen flask at reduced pressure, to yield three fractions. The fraction showing a boiling point of 166°-167°/mm contained the above-named product.

EXAMPLE 29

Preparation of 3-Ethyl-2,3,4,5-tetrahydro-7,8-Methylenedioxy-1H-3-benzazepine 11.68 g (0.05 M) of 3-acetyl-2,3,4,5-tetrahydro-7,8-methylenedioxy-1H-3-benzazepine was dissolved in 150 ml of dry tetrahydrofuran (THF) and the solution cooled to 5°. To the stirred solution (under nitrogen) 150 ml of a one-molar solution of borane in THF was added during the course of a few minutes; no temperature effect was noticeable. After the addition of the borane, the solution was heated to reflux; a gelatinous precipitate appeared soon after the reflux started. After refluxing for two hours the reaction vessel was cooled in an ice bath and 100 ml of 3N hydrochloric acid added dropwise to destroy the excess borane and the amine-boron complex.

After heating under reflux for an hour, the condenser was set for downward distillation, and the organic solvents removed by distillation. The cooled residue in water was made strongly alkaline, and the base extracted with three 250-ml portions of benzene. After drying and distillation of the solvent in the rotary evaporator, there remained a pale colored oil. This was dissolved in 20 ml of benzene and the solution passed over 50 g of $Al_2O_3$ (I), washing the adsorbent with 300 ml of benzene. Distillation of the solvent left a colorless oil that rapidly crystallized to yield the above-named product, m.p. 65°-66°.

The free base was converted to the hydrochloride in the usual manner and after recrystallizing from i-PrOH-$H_2O$ it melted at 268°-269° (dec).

EXAMPLE 30

Preparation of 3-Allyl-2,3,4,5-tetrahydro-7,8-methylenedioxy-1H-3-benzazepine hydrochloride To 5.7 g of 2,3,4,5-tetrahydro-7,8-methylenedioxy-1H-3-benzazepine (0.03 moles) in 75 ml of dimethylformamide was added 1.5 g of sodium hydride (0.034 moles). The suspension was stirred at 55°-60° until no more hydrogen was evolved. To the suspension, at room temperature, was added 4 g of allyl bromide in 25 ml of DMF. The suspension was stirred for 8 hours at 55°-60°, then at room temperature for a further 12 hours after which it was poured into 500 ml of water. The suspension was shaken with 100 ml of benzene and the lyers separated. The benzene layer was washed with NaCl solution and with water. After drying the benzene layer, the solvent was evaporated to yield the crude crystalline base. A sample was recrystallized from 60°-90° petroleum ether to yield the above-named product, m.p. 83.5°-85.5°.

The above base was converted to the hydrochloride in isopropanol with hydrochloric acid. After one recrystallization from aqueous isopropanol, the m.p. was 267.5°-268.5°(dec).

EXAMPLE 31

Preparation of 3-(3-Dimethylaminopropyl)-2,3,4,5-tetrahydro-7,8-methylenedioxy-1H-3-benzazepine hydrochloride The free base was prepared from 1.9 g of 2,3,4,5-tetrahydro7,8-methylenedioxy-1H-3-benzazepine (0.01 moles), 0.49 g of sodium hydride (0.011 moles), and 2.42 g of 3-dimethylaminopropyl chloride in 15 ml of dimethylformamide in the same manner as described for 3-allyl-2,3,4,5-tetrahydro-7,8-methylenedioxy-1H-3-benzazepine hydrochloride. After treating the reaction mixture with water and extracting with ether (6 × 25 ml) a yellow oil was obtained. This oil was converted to the hydrochloride and the salt recrystallized from EtOH-EtOAc twice to yield the abovenamed product as a white solid, m.p. 273°-275° (dec).

EXAMPLE 32

Preparation of 2,3,4,5-Tetrahydro-7,8-methylenedioxy-1H-3-benzazepine-3-butyric acid hydrochloride A. Preparation of the ethyl ester of the above-named free base 4.54 g (0.02 mole) of 2,3,4,5-tetrahydro-7,8-methylenedioxy-1H-3-benzazepine hydrochloride was suspended in 40 ml of dry dimethylformamide and to this was added in several portions, 1.95g (0.042 moles) of a 54% sodium hydride dispersion in mineral oil. On warming to 50°-60°, hydrogen was evolved and after two hours, the evolution of hydrogen ceased. To this mixture 4.30 g (0.022 moles) of ethyl 4-bromobutyrate was added in one portion and the mixture maintained at 50°-60° for another eight hours. The cooled reaction mixture was poured into 200 ml of ice water and the aqueous phase extracted four times with 50-ml portions of ether. After drying the ether phase (MgSO$_4$), the solvent was removed on the rotary evaporator. The oil thus obtained was dissolved in 10 ml of benzene and the solution passed over 50 g of Al$_2$O$_3$ (grade I).

B. Preparation of the amino acid hydrochloride

The oil recovered from the Al$_2$O$_3$ treatment (7 g) was dissolved in 10 ml of ethanol and added to a solution of 1.84 g of sodium hydroxide in 10 ml of water. After refluxing for 4 hours, the alcohol was distilled, the pH of the remaining solution brought to 3, and the solution evaporated to dryness. The solid residue was extracted several times with boiling ethanol and the combined extracts evaporated to dryness. The residue was recrystallized from a mixture of ethanol and ethyl acetate and yielded after chilling the above-named product, m.p. 245°-247° (dec).

EXAMPLE 33

Preparation of 2,3,4,5-Tetrahydro-7,8-methylenedioxy-1H-3-benzazepine-3-acetic acid A. The ethyl ester 45.4 g (0.2 moles) of 2,3,4,5-tetrahydro-7,8-methylenedioxy-1H-3-benzazepine hydrochloride was suspended in 250 ml of dry dimethylformamide. To this was added the sodium hydride obtained by washing the mineral oil from 19.5 g (0.42 moles) of a 54% sodium hydride-mineral oil dispersion; 50 ml of dimethylformamide being used to rinse the hydride into the reaction vessel. The temperature was slowly raised to 50°, whereupon hydrogen evolution commenced, and after two hours at 50°-60° it has practically ceased. The suspension was cooled in an ice bath and 27.0 g of ethyl chloroacetate added in one portion. The mixture was stirred at 60° for 8 hours, then cooled and poured into one l. of ice water. The oil that separated was extracted with five 200-ml portions of benzene, the combined extracts washed with water and dried (MgSO$_4$). Distillation of the solvent in the rotary evaporator gave 41 g of dark oil. This oil was dissolved in 100 ml of benzene and the solution passed over a column of 250 g of Al$_2$O$_3$(Woelm I). From the effluent, 20 g of a yellowish oil was recovered. Distillation of this oil gave 14 g of pale yellow oil, b.p. 153°-164°/0.3 mm that rapidly solidified. A small sample was recrystallized from ethanol, to yield 2,3,4,5-tetrahydro-7,8-methylenedioxy-1H-3-benzazepine-3-acetic acid ethyl ester, m.p. 89°-90°.

B. 6.0 of the above ester was refluxed with 30 ml of hydrochloric acid and 90 ml of water for four hours. Distillation of the solvent in the rotary evaporator left a residue of white salt. This was recrystallized twice from aqueous ethanol to yield the above-named product, m.p. 265°-267° (dec.)

Example 34

Preparation of 2,3,4,5-Tetrahydro-7,8-methylenedioxy-1H-3-benzazepine-3-ethanol and the corresponding hydrochloride 6.4 g (0.023 moles) of 2,3,4,5-tetrahydro-7,8-methylenedioxy-1H-3-benzazepine-3-acetic acid ethyl ester in 50 ml of ether was added to a stirred suspension of 2.18 g (0.0575 moles) of lithium aluminum hydride in 75 ml of ether, the entire operation being conducted in a nitrogen atmosphere. Sufficient heat was evolved to cause the ether to boil, and after the addition was complete, the stirred suspension was refluxed for another two hours. The excess hydride and the complex were decomposed with water in the usual way. A few g of filter aid were added to the mixed oxides and the solids removed on a bed of filter aid. Distillation of the ether gave a crystalline residue. The filter cake of oxides was refluxed with 100 ml of benzene and refiltered. From the filtrate, additional crystalline material was obtained. A sample of the product was recrystallized from petroleum ether, b.p. 60°-90°, to yield the above-named product, m.p. 112°-113°.

The hydrochloride was prepared in the usual manner and after recrystallization from isopropanol, it melted at 223°-225° (dec).

EXAMPLE 35

Preparation of N,N-Diethyl-2,3,4,5-tetrahydro-7,8-methylenedioxy-1H-3-benzazepine-3-acetamide hydrochloride 3.8 g of 2,3,4,5-tetrahydro-7,8-methylenedioxy-1H-3-benzazepine (0.02 moles) was suspended in 50 ml of DMF and the sodium hydride obtained by washing the mineral oil from 0.98 g of a 54% dispersion added thereto. The mixture was heated and stirred at 55°-60° for 2 hrs, after which hydrogen evolution ceased. To this suspension, 6 g of N,N-diethyl-2-chloroacetamide in 20 ml of DMF was added, and the suspension stirred for another eight hours at 55°-60°. After cooling, the mixture was cautiously treated with water (150 ml) and the base recovered by extraction with ether (6 × 75 ml). Distillation of the dried ether extract in the rotary evaporator gave a yellowish oil that was dissolved in anhydrous ether and the resulting solution acidified with ethereal HCl. The above-named product was obtained as a white salt by filtration, m.p. 233°-234°. After one recrystallization from EtOAc-i-PrOH, the m.p. was 238°-240° (dec).

EXAMPLE 36

Preparation of 3-[3-(4-Fluorobenzoyl)propyl]-2,3,4,5-tetrahydro-7,8-methylenedioxy-1H-3-benzazepine hydrochloride The sodium hydride obtained by washing 1.95 g of the 54% dispersion (0.042 moles) with benzene was used to prepare the sodium salt from 4.54 g. of 2,3,4,5-tetrahydro-7,8-methylenedioxy-1H-3-benzazepine hydrochloride in 50 ml of DMF as described in Example 35. Treatment of the suspension with 4.41 g of 3-(4-fluorobenzoyl)propyl chloride (0.022 moles) for 24 hours at 55°-60° followed by decomposition with 200 ml of ice water gave an oil-water suspension. The base was recovered by extraction with benzene (3 × 50 ml), the combined extracts washed once with water, then dried, and the solvent distilled in the rotary evaporator. To the residual oil, 3N hydrochloric acid was added and the mixture digested for an hour. After cooling the salt was filtered off, mp 195°14 197°. Two further recrystallizations from water gave the above-named product as a buff colored salt, mp 209°-210°.

EXAMPLE 37

Preparation of 3-Chloroacetyl-2,3,4,5 tetrahydro-7,8-methylenedioxy1H-3-benzazepine One-tenth mole, 22.7 g, of 2,3,4,5-tetrahydro-7,8-methylenedioxy-1H-3-benzazepine was dissolved in 200 ml of water and 200 ml of benzene added. Forty ml of a 10% solution of sodium hydroxide was added to the vigorously stirred emulsion and 17 g (0.15 mole) of chloroacetyl chloride was added dropwise. As the pH approached 5, another 10-ml portion of 10% sodium hydroxide solution was added until a total of 100 ml has been added. After all the chloroacetyl chloride had been added, the mixture, which has an acid reaction, was stirred for another 10 minutes then allowed to stand overnight at room temperature.

The mixture of solid and two liquid phases was filtered to recover the solid; it was washed with water and air dried. The benzene solution was separated, washed to neutrality with water, dried, and the solvent removed in the rotary evaporator.

The solids were combined and recrystallized from approximately 300 ml of isopropanol. After standing overnight at room temperature, the mixture was cooled in an ice bath for three hours. The crystals that separated were filtered off, washed with a little isopropanol and dried to yield the above-named product, m.p. 125°-126.5°.

EXAMPLE 38

Preparation of 2,3,4,5-Tetrahydro-3-methylaminoacetyl-7,8-methylenedioxy-1H-3-benzazepine hydrochloride 13.5 g (0.05 mole) of 3-chloroacetyl-2,3,4,5-tetrahydro-7,8-methylenedioxy-1H-3-benzazepine was dissolved in 250 ml of dry tetrahydrofuran and the solution added to approximately 150 ml of liquid methylamine at −78°. The mixture was stirred for 20 hours allowing the temperature to rise to 22° during this interval after which it was warmed on the steambath to drive out the excess methylamine. The white solid that had formed was filtered off and washed with tetrahydrofuran. Distillation of the solvent in the rotary evaporator left 18.2 g of a thick yellow syrup which was dissolved in a minimum of hot isopropanol. Chilling gave a white salt, mp 250°-252° dec. The salt was dissolved in 30 ml of hot methanol, the solution filtered and diluted with 210 ml of ethyl acetate. On standing at room temperature white crystals of the above-named product separated, mp 253°-254°(dec.).

EXAMPLE 39

Preparation of 3-[2-($\alpha,\alpha,\alpha$-Trifluoro-m-tolyl)acetyl]-2,3,4,5-tetrahydro-7,8-methylenedioxy-1H-3-benzazepine 6.0 g of $\alpha,\alpha,\alpha$-trifluoro-m-tolyl acetyl chloride (0.027 moles) was dissolved in 50 ml of dry benzene and added dropwise to a stirred solution of 2,3,4,5-tetrahydro-7,8-methylenedioxy-1H-3-benzazepine, 12.8 g (0.067 mole) in 50 ml of benzene at T<40°. After 30 minutes of stirring the suspension of white crystals, the mixture was transferred to a separatory funnel, washed several times with water, the organic phase dried (MgSO$_4$) and then distilled in the rotary evaporator. The crude solid was recrystallized from 60°-90° petroleum ether to give the above-named product, mp 102°-104°.

EXAMPLE 40

Preparation of N-(3,4-Methylenedioxy-phenethyl)phthalimide

Forty-one g of 3,4,-methylenedioxyphenethylamine (0.25 moles) was refluxed with 36 g of phthalic anhydride (0.28 moles) and 65 ml. of acetic acid for 2.5 hours. The mixture was cooled whereupon it solidified. The solid mass was broken up and triturated with water and the solid recovered by filtration. Recrystallization from 300 ml of acetic acid and 125 ml of water gave white crystals of the above-named product, m.p. 139°-140.5°.

EXAMPLE 41

Preparation of N-[3-(3,4-Dimethoxyphenyl)propyl]phthalimide 6.4 g of 3-(3,4-dimethoxyphenyl)-propylamine (0.03 moles) was refluxed with 5.47 g of phthalic anhydride (0.037 moles) in 70 ml of acetic acid for 2.5 hours. The solvent was then removed in the rotary evaporator. Recrystallization of the residue from 150 ml of ether gave 4.0 g of a first crop, m.p. 82°-85° and 7.0 g of a second crop, m.p. 81°-83°.

EXAMPLE 42

Preparation of 2-(3-Phthalimidepropyl)-4,5-dimethoxybenzyl chloride 3.25 g of N-[3-(3,4-dimethoxyphenyl)propyl]phtholimide (0.01 mole) was dissolved in 28 ml of chloroform and 2.25 g of paraformaldehyde (0.075 moles) added thereto along with 0.6 ml of concentrated hydrochloric acid. The mixture was vigorously stirred at −20° to −25° as a stream of hydrogen chloride was passed through. After two hours the mixture, which consisted of two liquid phases, was poured into 40 ml of ice water, the chloroform phase removed, and the aqueous layer extracted once with 20 ml of chloroform. The combined chloroform layers were washed three times with 40 ml portions of ice water, dried, and the solvent distilled in the rotary evaporator. The solid residue was recrystallized from a mixture of ethyl acetate/petroleum ether (60°-90°) to yield the above-named product, m.p. 150°-153°.

EXAMPLE 43

7,8-Methylenedioxy-2,3,4,5-tetrahydro-1H-3-benzazepine was prepared in the form of several pharmacological formulations as follows:

| A. Tablet Formulation | Per Tablet |
|---|---|
| 7,8-Methylenedioxy-2,3,4,5-tetrahydro-1H-3-benzazepine | 100 mg |
| Lactose, U.S.P. | 202 mg |
| Corn Starch, U.S.P. | 80 mg |
| Amijel BO11 | 20 mg |
| Calcium Stearate | 8 mg |
| Total Weight | 410 mg |

PROCEDURE 1. 7,8-Methylenedioxy-2,3,4,5-tetrahydro-1H-3-benzazepine, lactose, corn starch, and Amijel BO11 were blended in a suitable mixer.
2. The mixture was granulated to a heavy paste with water and the moist mass was passed through a No. 12 screen. It was then dried overnight at 110° F.
3. The dried granules were passed through a No. 16 screen and transferred to a suitable mixer. The calcium stearate was added and mixed until uniform.
4. The mixture was compressed at a tablet weight of 410 mg. using tablet punches having a diameter of approximately ⅜ inch. (Tablets may be either flat or biconvex and may be scored if desired).

*A prehydrolyzed food grade corn starch. Any similar prehydrolyzed corn starch may be used. Purchased from: Corn Products Company, 10 East 56th Street, NY, NY.

| B. Tablet Formulation | Per Tablet |
|---|---|
| 7,8-Methylenedioxy-2,3,4,5-tetrahydro-1H-3-benzazepine | 25.00 mg. |
| Dicalcium Phosphate Dihydrate, Unmilled | 175.00 mg. |
| Corn Starch | 24.00 mg. |
| Magnesium Stearate | 1.00 mg. |
| Total Weight | 225.00 mg. |

PROCEDURE:

1. 7,8-Methylenedioxy-2,3,4,5-tetrahydro-1H-3-benzazepine and corn starch were mixed together and passed through an No. 00 screen in Model "J" Fitzmill with hammers forward.
2. This remix was then mixed with dicalcium phosphate and one-half of the magnesium stearate, passed through a No. 1A screen in Model "J" Fitzmill with knives forward, and slugged.
3. The slugs were passed through a No. 2A plate in a Model "D" Fitzmill at slow speed with knives forward, and the remaining magnesium stearate was added.
4. The mixture was mixed and compressed.

| C. Capsule Formulation | Per Capsule |
|---|---|
| 7,8-Methylenedioxy-2,3,4,5-tetrahydro-1H-3-benzazepine | 50 mg. |
| Lactose, U.S.P. | 125 mg. |
| Corn Starch, U.S.P. | 30 mg. |
| Talc, U.S.P. | 5 mg. |
| Total Weight | 210 mg. |

PROCEDURE:

1. 7,8-Methylenedioxy-2,3,4,5-tetrahydro-1H-3-benzazepine was mixed with lactose and corn starch in a suitable mixer.
2. The mixture was further blended by passing through a Fitzpatrick Comminuting Machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

| D. Capsule Formulation | Per Capsule |
|---|---|
| 7-8-Methylenedioxy-2,3,4,5-tetrahydro-1H-3-benzazepine | 10 mg. |
| Lactose, U.S.P. | 165 mg. |
| Corn Starch, U.S.P. | 30 mg. |
| Talc, U.S.P. | 5 mg. |
| Total Weight | 210 mg. |

PROCEDURE:

1. 7,8-Methylenedioxy-2,3,4,5-tetrahydro-1H-3-benazepine, lactose and corn starch were mixed in a suitable mixer.
2. The mixture was further blended by passing through a Fitzpatrick Comminuting Machine with a No. 1A screen with knives forward.
3. The blended powder was returned to the mixer, the talc added and blended thoroughly.
4. The mixture was filled into No. 4 hard shell gelatin capsules on a Parke Davis capsulating machine. (Any similar type capsulating machine may be used).

EXAMPLE 44

The formulations of Example 43 were repeated using:
2,3,4,5-tetrahydro-3-methyl-7,8-methylenedioxy-1H-3-benzazepine; and
3-ethyl-2,3,4,5-tetrahydro-7,8-methylenedioxy-1H-3-benzazepine.

We claim:

1. A compound selected from the group consisting of compounds of the formula

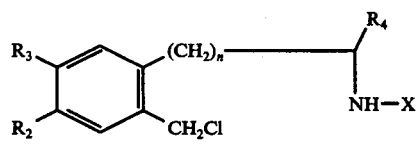

wherein $R_2$ and $R_3$ taken together signify methylenedioxy; $R_4$ signifies hydrogen, lower alkyl, carboxy, aryl or aryl substituted by a member selected from the group consisting of halogen, lower alkyl, nitro, or trifluoromethyl; n is 1 or 2; and X is acetyl.

2. N-6-Chloromethyl-3,4-methylenedioxyphenethyl) acetamide.

* * * * *